United States Patent
Dutra E Mello et al.

(10) Patent No.: US 9,216,377 B1
(45) Date of Patent: Dec. 22, 2015

(54) METHOD AND SYSTEM FOR REMOVING IMPURITIES FROM GAS STREAMS USING ROTATING PACKED BEDS

(71) Applicant: CHEVRON U.S.A. INC., San Ramon, CA (US)

(72) Inventors: Marcus V. Dutra E Mello, Moraga, CA (US); Fermin Rodriguez, Humble, TX (US); Hua-Min Huang, Hercules, CA (US); Manuel Lim, Walnut Creek, CA (US); Kelly James Conner, Seabrook, TX (US)

(73) Assignee: Chevron U.S.A. Inc., San Ramon, CA (US)

( * ) Notice: Subject to any disclaimer, the term of this patent is extended or adjusted under 35 U.S.C. 154(b) by 0 days.

(21) Appl. No.: 14/630,480

(22) Filed: Feb. 24, 2015

(51) Int. Cl.
*B01D 53/14* (2006.01)
*C10L 3/10* (2006.01)
*C07C 7/11* (2006.01)

(52) U.S. Cl.
CPC ........ *B01D 53/1493* (2013.01); *B01D 53/1425* (2013.01); *B01D 53/1475* (2013.01); *C07C 7/11* (2013.01); *C10L 3/103* (2013.01); *C10L 3/104* (2013.01); *C10L 3/106* (2013.01); *B01D 2252/20484* (2013.01)

(58) Field of Classification Search
CPC .... B01D 53/185; B01D 53/1456; B01D 3/08; B01D 3/30
See application file for complete search history.

(56) References Cited

U.S. PATENT DOCUMENTS

| | | |
|---|---|---|
| 5,832,712 A | 11/1998 | R.o slashed.nning et al. |
| 6,228,145 B1 | 5/2001 | Falk-Pedersen et al. |
| 8,540,871 B2 | 9/2013 | Zhan et al. |
| 8,702,071 B2 | 4/2014 | Mello et al. |
| 2005/0116364 A1 | 6/2005 | Gardner et al. |
| 2007/0034565 A1 | 2/2007 | Park |
| 2011/0126715 A1 | 6/2011 | Kimura |
| 2011/0131937 A1 | 6/2011 | Ming et al. |
| 2011/0296985 A1 | 12/2011 | Buhrman et al. |
| 2011/0303088 A1 | 12/2011 | Dutra E Mello et al. |
| 2012/0061613 A1 | 3/2012 | Heldebrant et al. |
| 2012/0175241 A1 | 7/2012 | Strand et al. |
| 2014/0047979 A1* | 2/2014 | Eimer et al. .................. 95/151 |
| 2014/0114110 A1* | 4/2014 | Mak .............................. 585/802 |
| 2014/0250945 A1* | 9/2014 | Huntington et al. ............ 62/602 |

FOREIGN PATENT DOCUMENTS

| | | |
|---|---|---|
| CN | 2870957 Y | 2/2007 |
| CN | 101219330 A | 7/2008 |
| CN | 201648002 U | 1/2010 |
| CN | 102151476 A | 8/2011 |
| CN | 103111177 A | 5/2013 |
| CN | 203212538 U | 9/2013 |
| CN | 103463938 A | 12/2013 |

(Continued)

*Primary Examiner* — Duane Smith
*Assistant Examiner* — Cabrena Holecek
(74) *Attorney, Agent, or Firm* — Gregory L. Porter; Andrews Kurth LLP (57) ABSTRACT

The present invention relates to a method and system for removing an impurity from a feed gas stream. Various embodiments include, for example, using a rotating packed bed, a pressure reducing device such as a turbine and/or control valve, a regenerator, and novel internal seal designs and liquid distributors. Advantageously, at least a portion of any energy produced is recycled for use in the process or elsewhere.

20 Claims, 7 Drawing Sheets

(56) References Cited

FOREIGN PATENT DOCUMENTS

| | | |
|---|---|---|
| CN | 103463954 A | 12/2013 |
| CN | 103480259 A | 1/2014 |
| CN | 203447959 U | 2/2014 |
| CN | 203447973 U | 2/2014 |
| CN | 203447974 U | 2/2014 |
| EP | 0084410 | 7/1983 |
| EP | 0020055 B1 | 12/1986 |
| GB | 2491177 A | 11/2012 |
| WO | 2012076658 A1 | 6/2012 |
| WO | 2012092980 A1 | 7/2012 |
| WO | 2012092984 A1 | 7/2012 |
| WO | 2013166550 A1 | 11/2013 |

* cited by examiner

Liquid Distributor Ring

METHOD AND SYSTEM FOR REMOVING IMPURITIES FROM GAS STREAMS USING ROTATING PACKED BEDS

FIELD OF THE INVENTION

Embodiments disclosed herein relate to methods and systems for removing impurities in gas streams using rotating packed beds.

BACKGROUND AND SUMMARY

Rotatable packed bed technology is commonly employed to separate impurities from gas streams. Unfortunately, many of the known processes and systems require large amounts of energy, complex equipment, and often result in poor separation. It would be desirable to discover new methods and systems that used less energy, result in good separation, and could employ readily available equipment.

The present invention relates to new methods and systems for removing impurities in gas streams using rotating packed beds. Advantageously, the new methods and systems often use less energy, result in good separation, and/or could employ readily available equipment.

In one embodiment, the invention pertains to a method for removing an impurity from a feed gas stream. The method comprises contacting in a rotating packed bed absorber a liquid solution capable of absorbing an impurity and a feed gas comprising an impurity. The rotating packed bed absorber comprises a packed bed with one or more rotatable packing rings having an interior region within the packed bed. The absorber is characterized by (1) at least one liquid inlet for infusing liquid into the interior region of the packing bed, (2) at least one gas inlet for infusing a feed gas into the interior region of the packing bed via the chamber; (3) at least one gas outlet for removing gas from the interior region of the packing bed; and (4) at least one liquid outlet for removing liquid from the interior region of the packing bed. The contacting occurs under conditions such that the liquid solution absorbs impurity to produce an impurity-rich liquid solution. The impurity-rich liquid solution is removed and the pressure of the impurity-rich liquid solution is reduced. At least a portion of any energy produced is recovered.

In another embodiment the invention relates to a system for removing an impurity from a feed gas stream. The system comprises a rotating packed bed absorber with one or more rotatable packing rings. The absorber is configured for contacting a feed gas stream comprising one or more impurities with a liquid to produce (1) an impurity-rich liquid solution comprising one or more absorbed impurities and (2) purified gas. A pressure reducing device is in fluid communication with the rotating packed bed absorber for receiving and reducing the pressure of the impurity-rich liquid solution and recovering energy therefrom. At least some of the energy recovered in the pressure reducing device may be employed to rotate the one or more rotatable packing rings of the rotating packed bed absorber.

In yet another embodiment the invention pertains to a system for removing an impurity from a feed gas stream. The system comprises a rotating packed bed absorber with one or more rotatable packing rings. The absorber is configured for contacting a feed gas stream comprising one or more impurities with a liquid to produce (1) an impurity-rich liquid solution comprising one or more absorbed impurities and (2) purified gas. A pressure reducing device is in fluid communication with the rotating packed bed absorber for receiving and reducing the pressure of the impurity-rich liquid solution and recovering energy therefrom. A regenerator for regenerating the impurity-rich liquid solution is operably linked to the pressure reducing device for regenerating the impurity-rich liquid solution for reuse in the rotating packed bed absorber. The regenerator and pressure reducing device are configured such that at least some of the energy generated in the pressure reducing device may be employed in regeneration.

DETAILED DESCRIPTION

Feed Gases, Absorbents, and Impurities

The present invention pertains to removing impurities from a feed gas stream using one or more rotating packed beds. The method and systems described herein are broadly applicable to many different impurities and many different feed gas streams. Generally, any impurity or combination of impurities that are capable of being absorbed by a liquid absorbent in a rotating packed bed may be separated in the present methods and systems. Common impurities that may be separated from a feed gas stream include, for example, $H_2S$, $CO_2$, $H_2O$, various metals such as mercury (Hg), and mixtures thereof.

The absorbent employed in the systems and methods described herein is typically a liquid solution. The liquid solution will, of course, vary depending upon the impurities, feed gas, desired separation, equipment employed, and the like. Generally, the liquid solution may be any that is useful for removing acidic components in various hydrocarbon or other streams. In some embodiments, the liquid solution comprises an amine, a glycol, a physical solvent or even a mixture thereof. Physical solvents such as SELEXOL (mixture of the dimethyl ethers of polyethylene glycol), UCARSOL (a methyldiethanolamine-based product), PURISOL (NMP or N-Methyl-2-Pyrrolidone), and the like, as well as, hybrid processes such as SULFINOL (which uses a physical solvent, sulfolane, and chemical solvent such as diisopronaolamine (DIPA) and/or methyl diethanolamine (MDEA)) may be useful in removing impurities such as $H_2S$ and/or $CO_2$. For water removal, a glycol mixture such as triethylene glycol is usefully employed while $K_2CO_3$ (hot pot process) may often be employed in the removal of $CO_2$.

Similarly, the present methods and systems may be broadly applicable to many streams used in refineries, petrochemical plants, natural gas processing plants and other industries. A common feed gas to which the methods and systems are applicable includes, for example, produced natural gas that is predominantly $CH_4$ at pressures ranging typically from about 100, or about 300 to as much as about 2,000 psig or higher. Hydrogen streams containing $H_2S$, such as those that result from hydrotreating processes found in oil refineries are another common feed where rotating packed bed equipment such as that described herein can be used. The skilled artisan using the present disclosure will readily adjust the methods and systems described here depending upon the impurities to be removed, feed gas stream, absorbents, equipment employed, and other considerations.

Rotating Packed Bed Absorbers and Regenerators

The general method of the present invention usually first involves providing a rotating packed bed with one or more, two or more, or even three or more, rotatable packing rings. Such beds are well-known in the art and are sometimes referred to as Higee reactors or Higee technology. Exemplary reactors are described in, for example, U.S. Pat. No. 8,702, 071 and WO 2012/092981, which for U.S. patent practice are incorporated herein by reference.

The specific configuration of the rotating packed bed and the composition and number of rotatable packing rings will vary depending upon the application and desired results. Generally, the rings can be made of any porous materials which are compatible with the desired application. Often, high surface area, metal foam type materials are employed. The pore sizes of the material are considered when selecting material for a desired application. Commercial materials such as Ni—Cr alloy with 0.6 mm diameter may be useful for a broad range of applications. If metals such as Hg are to be removed in a rotating packed bed then usually the packing is coated with a suitable absorbent material for binding the desired metal.

Figure 4:
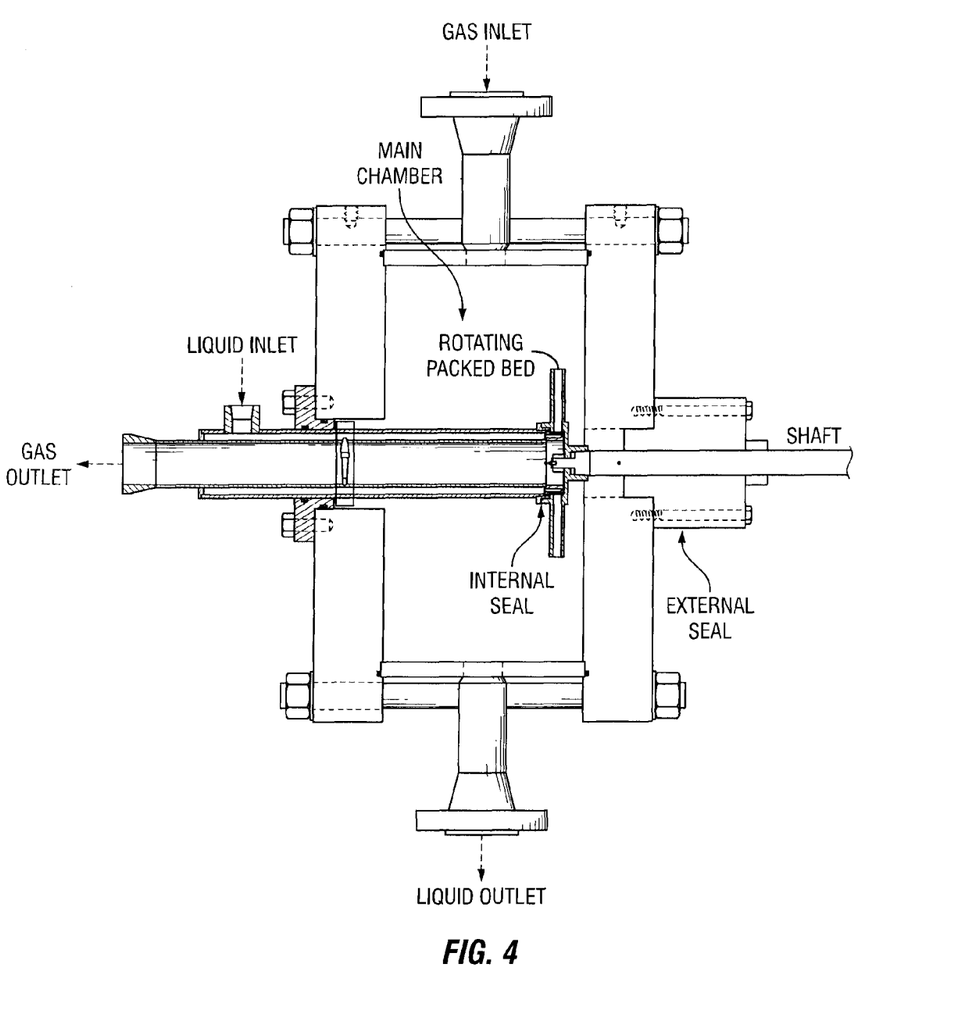
FIG. 4 depicts an embodiment of the invention illustrating a integrated liquid distributor/gas outlet of a representative Higee/Rotating Packed Bed.
Figure 7:
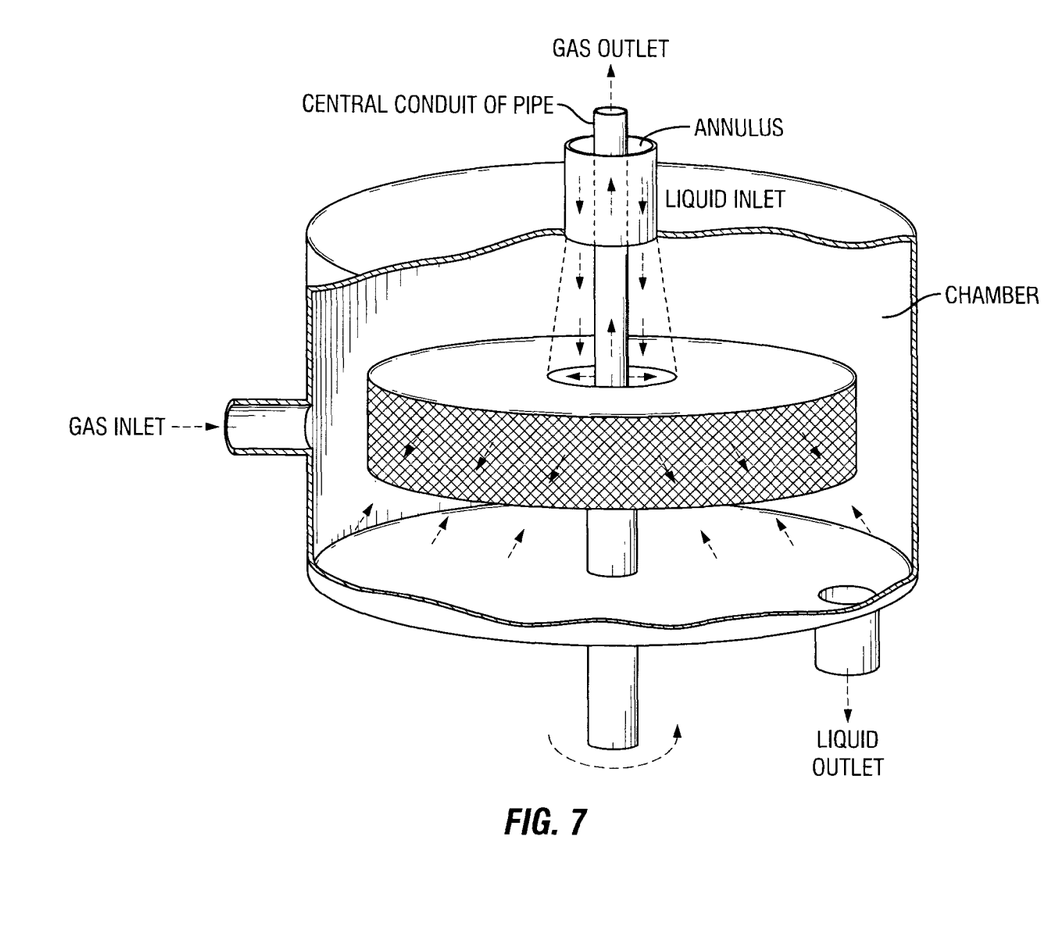
FIG. 7 depicts an embodiment of the invention illustrating a conventional rotating backed bed with an unsplit ring.

Typically, the packed bed is disposed within a main chamber as shown in, for example, FIG. 4. The bed may be in any suitable configuration and may vary depending upon the specific application. Specifically, the bed may be configured wherein it is a single, unsplit ring as shown in, for example, FIG. 7. Alternatively, the bed can be in a configuration where it is split in multiple rings wherein an interior region lies in between the split rings. Such a split packing configuration is described in, for example, U.S. Pat. No. 8,702,071, which for U.S. patent practice are incorporated herein by reference. In either configuration the contact between liquid and gas occurs in the interior region and/or the space within the packing and in the main chamber. For rotating packed bed absorbers the contacting is usually under conditions such that the liquid solution absorbs impurity to produce an impurity-rich liquid solution. On the other hand, for rotating packed bed regenerators the contacting is usually under conditions such that the impurity may be de-sorbed from the impurity-rich liquid solution to produce a liquid solution that can be reused in an absorber.

Typically, an absorber or regenerator will comprise a rotating packed bed, a liquid distributor, and a main chamber wherein the rotating packed bed is disposed within the main chamber. The configuration of the main chamber will depend upon the desired application and results. Generally, the main chamber is characterized by (1) at least one liquid inlet for infusing liquid into an interior region within the packing, (2) at least one gas inlet for infusing a feed gas stream into the interior region; (3) at least one gas outlet for removing gas from the interior region within the packing; and (4) at least one liquid outlet for removing liquid from the interior region within the packing. While we state that the gas inlet infuses a feed gas stream into the interior region it is typically accomplished by first infusing the feed gas into the chamber whereupon with sufficient pressure it is then forced into the interior region within the packing.

The one or more rotatable packing rings may be rotated by any convenient mechanism or manner. Typically, one or more motors are configured to rotate the one or more rotatable packing rings. If desired, one motor may be configured to drive two or more rotatable packing rings or even two or more rotating packed beds configured in parallel whether they be rotating packed bed absorbers or rotating packed bed regenerators. However, it is sometimes advantageous to have each set of rotatable packing rings operated by its own motor. In this manner, each set of rotatable packing rings may be operated independently. In the present invention a motor is optional because energy from the process is employed to, for example, rotate the one or more rotatable packing rings.

While the rotatable packing rings of an absorber or regenerator are rotating, a liquid solution is infused into the interior region of the rotatable packed bed. The solution may be infused in any convenient manner, which manner may depend upon the specific configuration. Generally, the liquid solution is infused by way of at least one or more liquid inlets into the interior region at substantially the same pressure of the gas feed. The size, shape, and construction of the one or more inlets may vary depending upon the equipment and the liquid employed. As described above, the liquid solution varies depending upon the impurities, feed gas, and equipment employed. The concentration, volume, pressure and flow rate of the infused liquid solution will also vary for similar reasons.

Generally, the liquid solution, concentration, and/or volume is selected such that the impurity or impurities are capable of being absorbed or desorbed as desired in the desired amounts. Typical flow rates may range from about 1 MMSCFD up to about 180 MMSCFD for the gas and from about 1 gpm up to about 1,000 gpm for the liquid.

Simultaneous or subsequent to the beginning of liquid solution infusion, in a typical absorption process a feed gas is injected into the chamber of the bed while the rotatable packing ring(s) is/are rotating at the desired speed. Such injection may be by any convenient manner, but is typically done through at least one gas inlet. The size, shape, and construction of the one or more gas inlets may vary depending upon the equipment and the gas or gases employed. In one embodiment, the configuration shown in FIG. 4 may be employed with either style of the two alternate internal seal designs depicted in FIG. 3 and described in detail below along with the liquid distributor. The one or more gas and liquid inlets are usually configured in a manner such that the liquid solution and feed gas or gases may pass within the packing in a manner such that the liquid solution and feed gas contact each other in the interior region within the packing.

The contact between the liquid solution and feed gas is typically orchestrated in a manner such that the desired type and amount of impurity or impurities is absorbed by the liquid solution. Typical contact time may vary, but for many applications the contact time generally ranges from milliseconds to less than about one (1) second. Typically, the absorbing comprises dissolving, dehydrating, gathering and/or reacting of the target impurity or impurities in a manner such that a majority (about 50, 60, 70, 80, 90, or even 99% or more) of the targeted impurity or impurities moves from the feed gas stream to liquid solution to produce an impurity-rich liquid solution. The purified gas may then be removed through the gas outlet in the liquid distributor and transferred as desired via pipeline or other methods.

The impurity-rich liquid solution may then be removed through one or more liquid outlets of the rotatable packed bed or beds. The size, shape, and construction of the one or more liquid outlets may vary depending upon the equipment and the composition of the impurity-rich liquid solution and other components employed. Typically, the process may be operated continuously however batch processing is possible as well. Once the impurity-rich liquid solution is removed through one or more liquid outlets, then the pressure of the impurity-rich liquid solution will be reduced prior to regeneration. The pressure reduction may be accomplished in any convenient manner which permits the recovery of energy simultaneous with the pressure reduction. The specific method used, of course, may vary depending upon the specific equipment and processes employed.

Pressure Reduction on the Impurity-Rich Liquid and Associated Energy Recovery

The pressure of the impurity-rich liquid solution is reduced prior to any regeneration in order to minimize the energy required to reboil the rich liquid during regeneration. Typically, in many processes the pressure is reduced from its pressure in the absorber which is generally from about 200 psig to about 2,000 psig to a reduced pressure which is from about 10 psig to about 20 psig. This pressure reduction is accomplished in a manner (described below) that allows for energy recovery. The resulting vapor/gas phase and the residual liquid are usually cooled to a temperature that corresponds to the reduced pressure.

The type of equipment employed for pressure reduction and subsequent energy recovery may vary depending upon the other equipment and how the recovered energy is to be utilized. A pressure reducing device is employed that allows the pressure to be controllably reduced in a manner such that energy from the pressure reduction may be recovered. As a result of this pressure reduction, at least a portion of the partially to fully saturated liquid and/or impurities (e.g., CO2, $H_2S$, water) in the rich liquid "flashes" into vapor/gas phase. Often a flash drum is employed to provide the needed volume for the disengagement of gas from the liquid. The pressure reducing device may comprise a turbine, a control valve, or a combination thereof.

Figure 1:
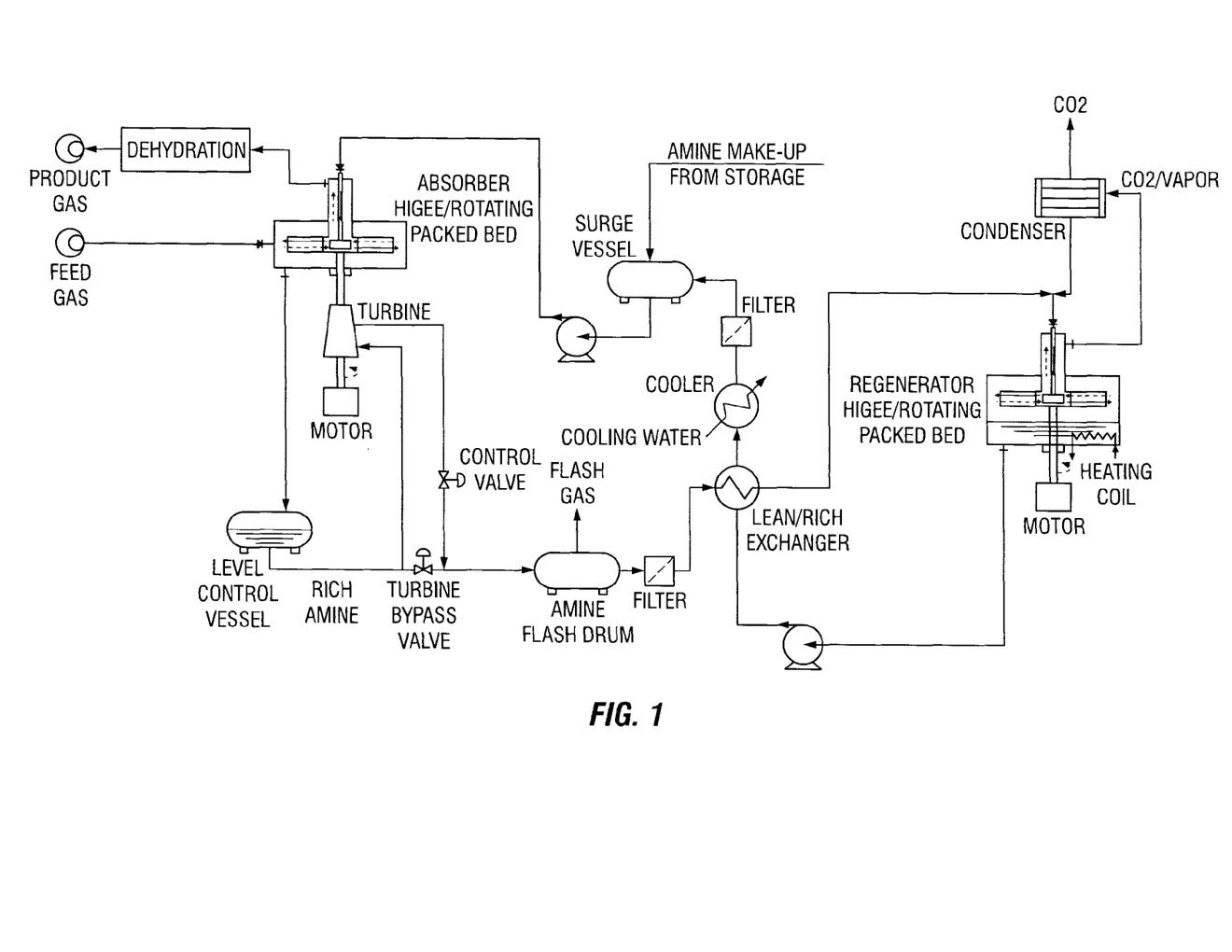
FIG. 1 depicts an embodiment of the invention illustrating energy recovered from liquid expansion and pressure reduction being used to drive a Higee rotating packed bed absorber.

In one embodiment, the pressure reducing device can be a hydraulic turbine combined with a control valve to regulate the turbine speed. The control valve usually does so by controlling the amount of liquid that is fed to the turbine. If desired, such a turbine may be operably connected to the one or more rotatable packing rings of the rotating packed bed, whether it be a rotating packed bed absorber or a rotating packed bed regenerator. In this manner, mechanical energy from the reduction in pressure may be recovered and employed in the process such as, for example, to rotate the one or more rotatable packing rings of the rotating packed bed as shown in FIG. 1 for the rotating packed bed absorber and in FIG. 2 for the rotating packed bed regenerator. Of course, the turbine could also be used to generate electrical power if desired.

Multiple rotating packed beds can be added in parallel to each other to handle higher gas flowrates. Such a plurality of beds can be employed for both the absorber and regenerator rotating packed beds. Potentially, the multiple set of rotating packed beds for one service (e.g., absorber) can be powered by a common shaft. That is, a common shaft may power two or more absorber rotating packed beds. Additionally or alternatively, a common shaft may power two or more regenerator rotating packed beds.

Figure 2:
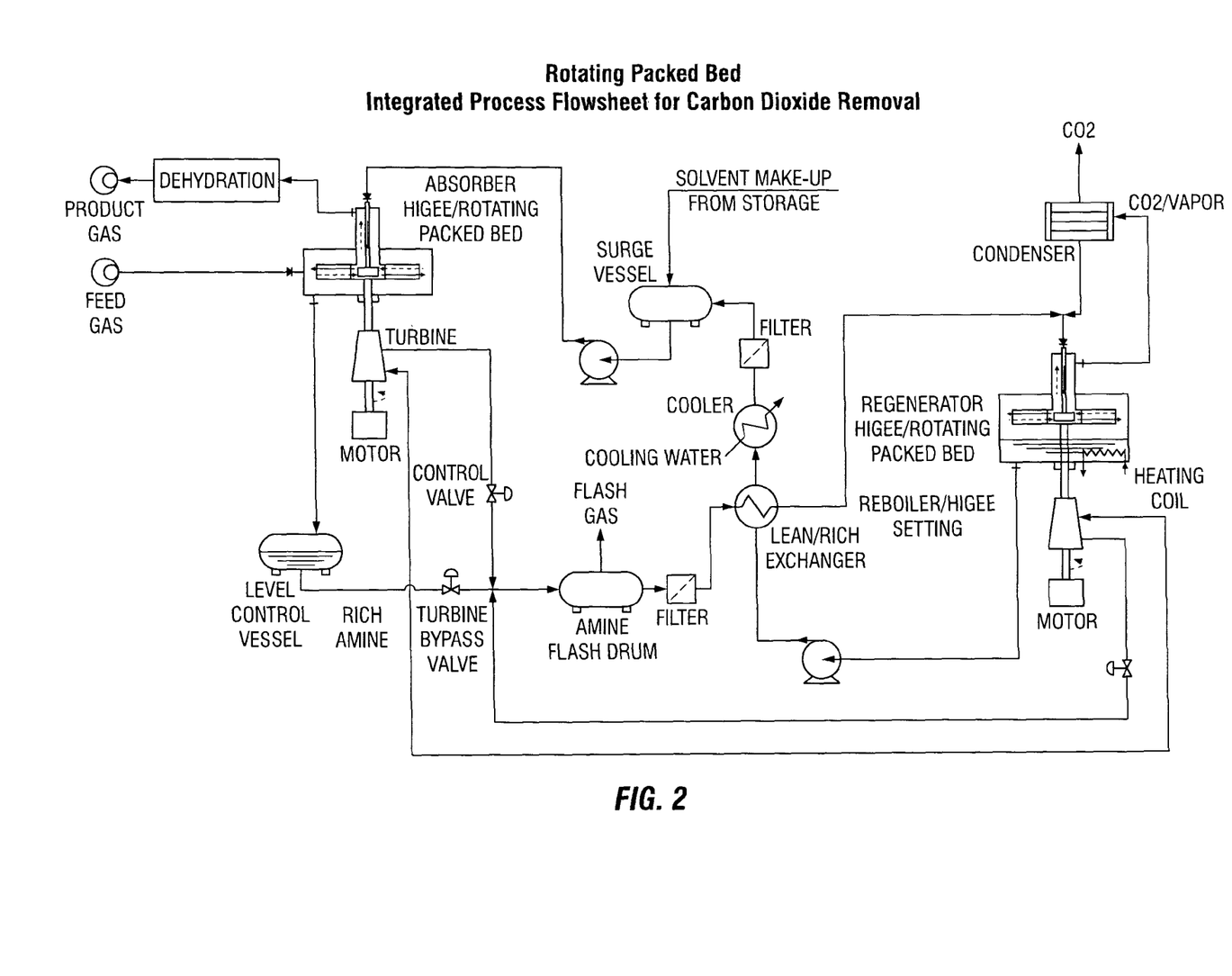
FIG. 2 depicts an embodiment of the invention illustrating energy recovered from liquid expansion and pressure reduction being used to drive (1) a Higee/rotating packed bed absorber and/or 2) a Higee rotating packed bed regenerator.

The recovered energy can power the absorber as shown in FIG. 1. Alternatively, the recovered energy can power the regenerator or both the absorber and regenerator as shown in FIG. 2. If a hydraulic turbine is utilized to power the rotating packed bed absorber or the regenerator, a control valve located on the discharge of the turbine as shown in FIGS. 1 and 2 will be used to regulate the turbine (and if on a common shaft, the absorber or regenerator rotating beds) shaft speed to the desired setpoint. Additionally, a separate valve, i.e., turbine bypass valve shown in FIGS. 1 and 2, may be installed parallel to the turbine and can be controlled either by flow or liquid level in the absorber or regenerator depending on system requirements. In this way, shaft speed and liquid flow/level can be independently controlled if desired.

The amount of available energy to the hydraulic turbine is directly proportional to the differential pressure between the absorber and flash drum shown in FIGS. 1 and 2 wherein the control valve is located between said absorber and flash drum. If the available horsepower is less than what is required by the absorber or regenerator, an optional additional variable speed motor can be used to supplement the additional required horsepower to maintain shaft speed.

Regeneration

Figure 6:
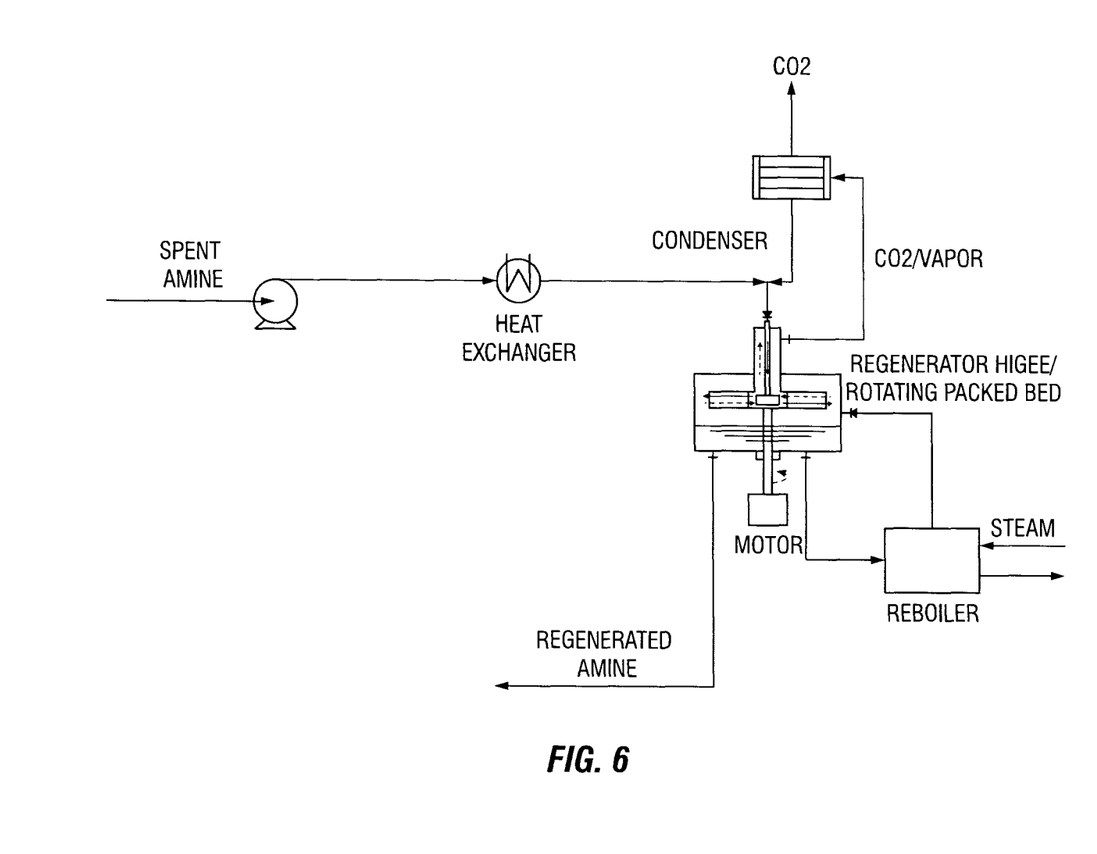
FIG. 6 depicts an embodiment of the invention illustrating use of an external reboiler in a Higee/Rotating packed bed regenerator.

If desired, the impurity-rich liquid solution removed from the absorber may be regenerated. Such regeneration may be by any convenient method and may use a regenerator for regenerating the impurity-rich liquid solution. The regenerator is operably linked to, for example, the flash drum and rotating packed bed absorber. In this manner the impurity-rich liquid may be delivered to a second (or more) rotating packed bed regenerator to be used for regeneration. The specific equipment of the regenerator may vary depending upon the specific process, other equipment, and available space. For example, the regenerator may comprise, for example, a heater, such as a reboiler and a condenser, one or more additional rotating packed bed regenerators, with one or more rotatable packing rings, or even some combination thereof. If desired, the heating or reboiler unit may be external to the rotating packed bed chamber (as shown in FIG. 6), or partially or fully integrated, i.e., inside the rotating packed bed chamber (as shown in FIGS. 1 and 2). In some embodiments, the regenerator may comprise a packed tower.

The above-described processes and systems may be advantageous for a number of independent reasons. For example, when using integrated processes and systems with rotating packed beds for absorption and/or regeneration, there is often less capital cost and a reduction of equipment weight and/or footprint (especially vertical) due to the compact nature of rotating packed beds. In addition, the processes and systems will usually bring about enhanced safety due to reduced liquid inventory, better operability due to potential foaming reduction, and often a high turn-down ratio. In addition, the substantial insensitivity to motion of rotating packed beds may be advantageous for offshore platforms, floating units, and the like. Yet another advantage may be in transportation and installation in remote areas. Usually, due to corrosion concerns, the amine loading is limited in a conventional vessel. However, due to the more compact nature of rotating packed beds which allows for the use of more expensive materials such as alloys, richer, i.e., more concentrated, increased amine loadings may be employed which may reduce circulation rates, which in turn may reduce operating costs.

FIGS. 1-2

FIG. 1 shows an illustrative embodiment wherein contaminants are removed from a feed gas. The feed gas comprising $CO_2$ and/or other impurities is injected through a gas inlet into a rotating packed bed absorber where it contacts a liquid amine or other solvent solution from a surge vessel which is simultaneously infused into the rotating packed bed absorber through a liquid inlet in a liquid distributor. The rotating packed bed comprises one or more rotatable packing rings having an interior region within the packing which is disposed within a chamber characterized by (1) at least one liquid inlet for infusing liquid into the interior region within the packing, (2) at least one gas inlet for infusing a feed gas into the interior region; (3) at least one gas outlet for removing gas; and (4) at least one liquid outlet for removing liquid. The contacting occurs under conditions such that the liquid solution absorbs impurity. Purified gas is removed from the rotating packed bed absorber through the gas outlet in the liquid distributor.

The regenerator is often a second rotating packed bed albeit a regenerator with a heating coil and condenser for regenerating the amine and/or solvent and returning it after cooling and filtering to a surge vessel for re-use. An optional motor may also be employed. If necessary make-up amine and/or other solvent may be added to the surge vessel for the continuous process. The regenerator can also be a packed tower as an alternate.

The method described in FIG. 2 is similar to FIG. 1 but includes a second turbine for use in the rotating packed bed regenerator that is part of the regenerator. In this manner, the energy that is recovered from the pressure reduction in the rotating packed bed absorber may be converted to shaft horsepower and used to drive the rotating packed bed absorber, the rotating packed bed regenerator, or both.

The impurity-rich liquid solution is removed through the liquid outlet and passed through a control valve and a hydraulic turbine wherein the pressure of the rich amine and/or other solvent is reduced before passing to an amine flash drum. While the flash drum is referred to as an amine flash drum here and in the figures it should be understood that other solvents besides amines may be employed in the methods and systems described here. As shown in FIGS. 1 and 2, the energy that is recovered is converted to shaft horsepower for the rotating packed bed absorber and/or rotating packed bed regenerator. An optional motor may be also connected to supplement any additional required horsepower and also be available for transient startup and shutdown conditions. Once the rich amine and/or other solvent is in the flash drum absorbed gases are flashed off as flash gas. The liquid solution is then filtered and directed to the regenerator.

Figure 3:
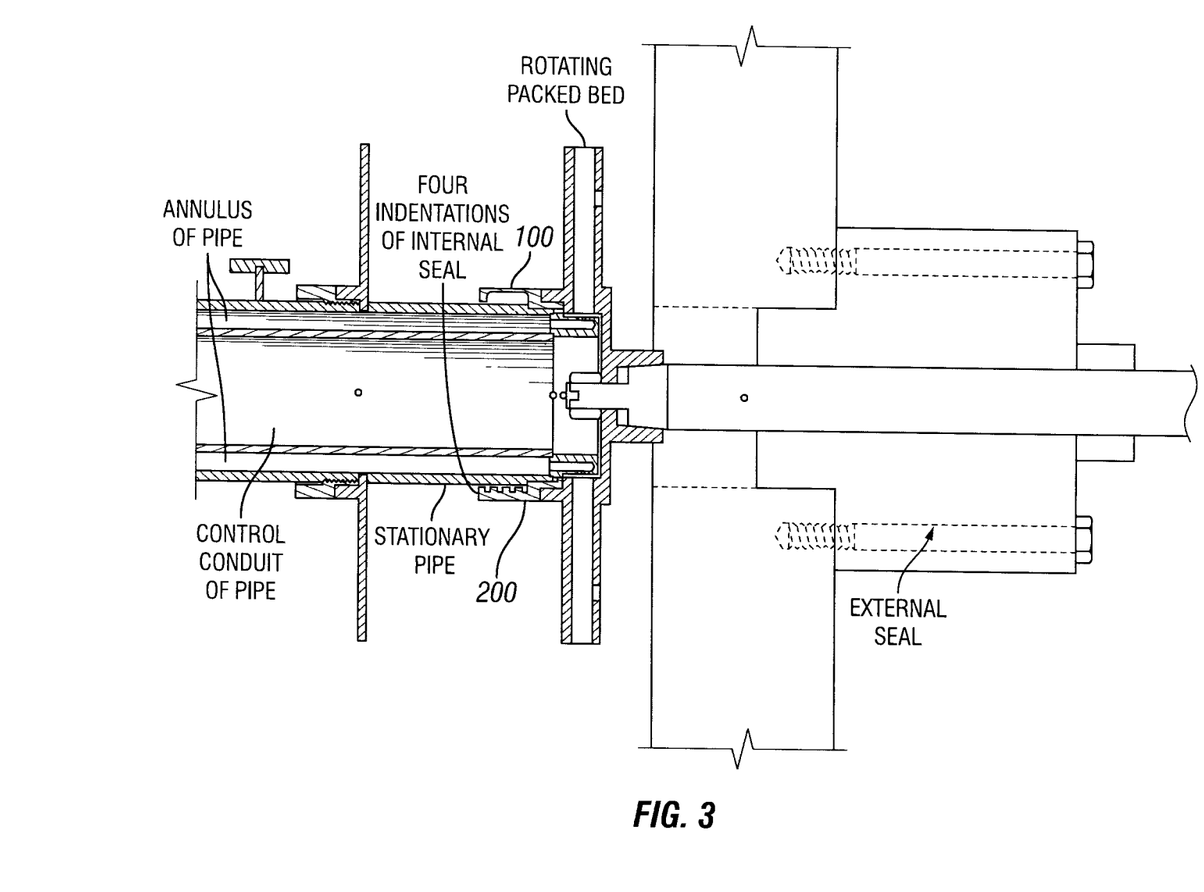
FIG. 3 depicts an embodiment of the invention illustrating internal seal designs in a liquid distributor of a representative Higee/Rotating Packed Bed.

Liquid Distributor and Internal Seals Shown in FIGS. 3 and 5

Figure 5A:
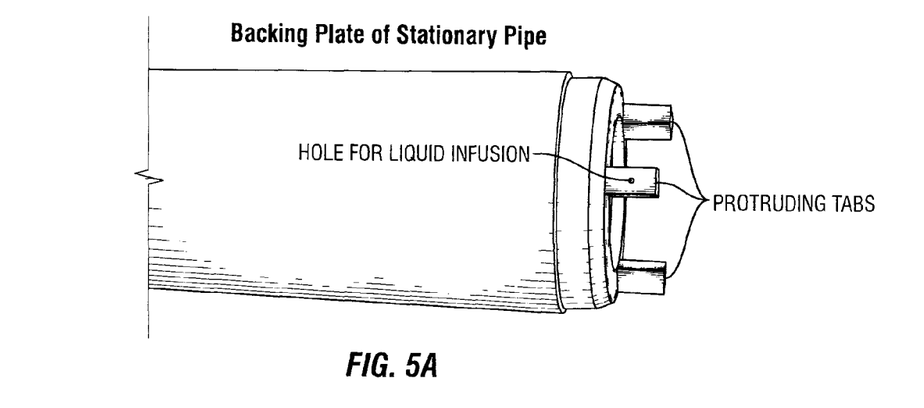
FIG. 5(a)-(d) depict various embodiments of the invention relating to the liquid distribution design of a rotating packed bed.
Figure 5B:
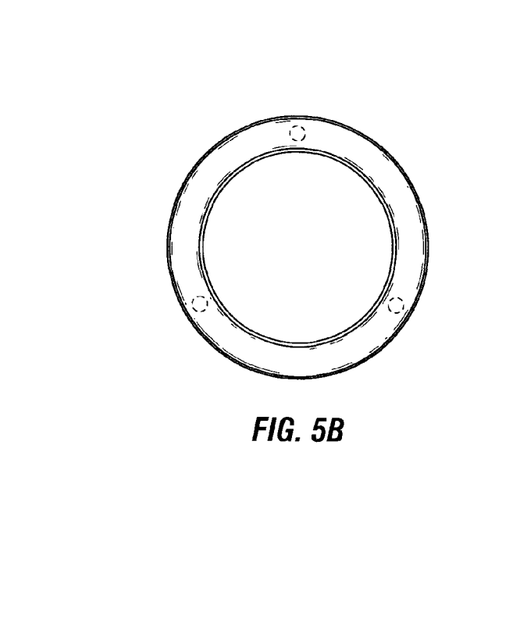
Figure 5C:
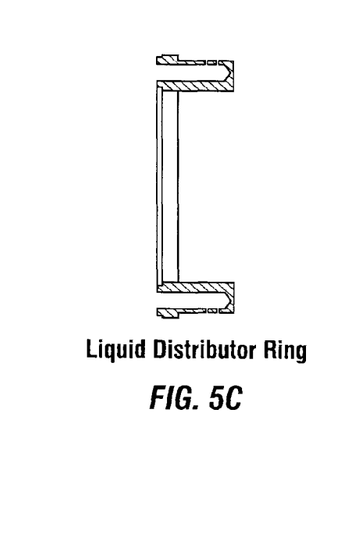
Figure 5D:
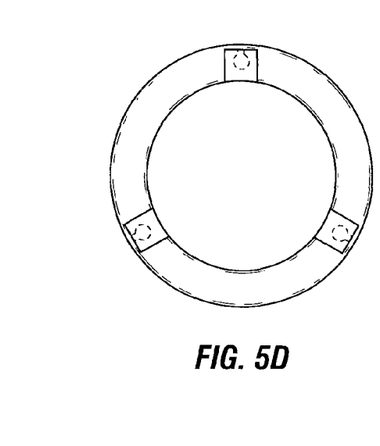

In one embodiment, liquid may be introduced into the rotating packed bed through the annulus of a stationary pipe, as depicted in FIG. 3. The central conduit of said pipe may preferably be used to remove purified product gas that leaves the chamber. As shown in FIG. 5(a), the stationary pipe may have, for example, three protruding tabs with two outward-facing holes drilled in the center of each tab for the liquid to be infused into the packing bed. As shown, each hole has 0.079" diameter and there is a total of 6 holes. Of course, the number of tabs, number of holes, their specific shape, and their dimensions may vary depending on the process. Generally, for higher flowrates more holes may be desirable. Another example of a liquid distribution system that can be employed is described in our U.S. Pat. No. 8,702,071.

Internal seals are shown in FIG. 3. Internal seals assist in avoiding bypass or flow of feed gas into the space between the rotating packed bed and the stationary pipe. The design of the internal seals depicted in FIG. 3 at 100 is one potential design. In some applications, a variation of that design which comprises added indentations to the seal design as shown in FIG. 3 at 200 may be beneficial. The seal design in FIG. 3 at 200 may be particularly useful in creating more resistance (higher pressure drop) and therefore minimize gas flow through that space. FIG. 3 also shows an external seal which is commercially available at, for example, John Crane Co.

Exemplary embodiments of the present disclosure are further illustrated by the following examples which should not be construed as limiting. The contents of all references, patents and published patent applications cited throughout this application, as well as any Figures or Tables are incorporated herein by reference.

Examples

The present invention is used to remove $CO_2$, $H_2S$ and/or $H_2O$ from such hydrocarbons as $CH_4$ or natural gas before the hydrocarbon is transported through a pipeline or fed to an LNG plant. For $CO_2$ and $H_2S$ removal, an amine may be selected from the group consisting of monoethanolamine (MEA), diethanolamine (DEA), methyldiethanolamine (MDEA), diisopropanolamine (DIPA), diglycolamine (DGA), piperazine, etc and combinations thereof to be used as the liquid solution. Proprietary solvents which contain one or more of the solvents cited above can also be used in this process (e.g., Dow's UCARSOL (a methyldiethanolamine-based product). Other solvents that can be used include: (1) Potassium carbonate (Hot Pot process), (2) Physical solvents such as SELEXOL (mixture of the dimethyl ethers of polyethylene glycol), PURISOL ((NMP or N-Methyl-2-Pyrrolidone) and the like. Hybrid processes such as Shell's SULFINOL which uses a physical solvent, sulfolane, and chemical solvent such as diisopronaolamine (DIPA) and/or methyl diethanolamine (MDEA)), which uses a combination of a physical solvent (sulfolane), and a chemical solvent, diisopropanolamine (DIPA) or methyl diethanolamine MDEA can also be used. For removal of $H_2O$, a glycol or glycol mixture is typically employed as the liquid solution.

The gas to be purified is injected into a rotating packed bed with one or more rotatable packing rings having an interior region within the rings. The gas may be injected at a pressure of at least about 100, preferably at least about 300, more preferably at least about 500 psig up to a pressure of less than about 2,500, preferably less than about 2,000, and more preferably less than about 1,500 psig. The rotating packed bed is disposed within a chamber characterized by (1) at least one liquid inlet for infusing liquid into the interior region within the packing, (2) at least one gas inlet for infusing a feed gas stream into the chamber whereupon the gas is forced into the interior region of the packing; (3) at least one gas outlet for removing gas; and (4) at least one liquid outlet for removing liquid.

The rotating packed bed may have a surface area/volume of from about 1,500 to about 5,400 $m^2/m^3$. The bed material can be any high surface area material, highly porous and with adequate mechanical strength to withstand high pressure and rotation.

In obtaining the data described in Tables 1-3 below a metal foam, an alloy material made of nickel and chromium with average pore size of 0.6 mm and surface area of at least 2,800 m2/m3 supplied by RECEMAT BV (model NCX2733.10) was employed as the bed material. Of course, different pore sizes and surface areas can be employed and, in general, a higher surface area will provide superior separation effectiveness to the expense of higher pressure drop or potential for increased plugging issues.

As described above, the bed(s) may be configured to comprise one rotatable packing ring (unsplit configuration) or multiple rotatable concentric rings (split configuration) which rings are attached to rotors that can either rotate in co-current, counter-current mode, or both. The concentric rings are located a suitable distance from each other so as to advantageously contribute to mass transfer enhancement. Each set of rings may spin at a speed of from about 200 to about 3000 rpm. Typically, an increase in speed of rotation may favorably impact the removal and/or release of the contaminants ($CO_2$, $H_2S$, or both and water).

A hydraulic or other turbine may receive any high pressure fluid (amine or glycol, or other solutions laid out above) from the liquid outlet of the rotating packed bed. Power may be recovered from this high pressure amine or glycol stream and the power may be used on other parts of the process, e.g., to drive the absorber and/or the regenerator rotating packed bed. A second hydraulic turbine can be used for driving the regenerator rotating packed bed. A low pressure outlet of the one or more turbines may be routed to a regenerator rotatable packed bed inlet.

Rotor speed for each rotating packed bed may be adjusted and/or controlled via inlet and/or outlet control valves. Turbine bypass control valves can be employed in transient start-up and shutdown conditions, as well as independently control the liquid level in the level control vessel. In the examples below rotating speeds of 500-2,500 rpm were employed in the absorber. Utilization of hydraulic turbines can assist in ensuring that operation of the rotating packed bed(s) may be independent from electrical power utility. In this manner one or more impurities may be removed from a feed gas stream as desired.

An internal seal (FIG. 3) is used to seal the space between the rotating packed bed/shaft and the stationary pipe. The said pipe is the conduit of fresh liquid into the unit (through its annulus part) and product gas exiting the unit after impurities have been scrubbed out. The product gas flows through the core part of the stationary pipe. The goal of the internal seal is to create enough pressure drop to force the vast majority of the gas flow to enter the packing, therefore preventing short-circuiting. Two different internal seal designs have been employed in the examples below and they are depicted as numeral 100 and 200 in FIG. 3. The two designs are similar with the exception that the seal at 200 has four indentations shaped like teeth that were machined into the seal material (TEFLON a synthetic fluoropolymer of tetrafluoroethylene) to further increase the resistance for gas to take that path rather than through the packing where the contact with fresh liquid is bound to take place.

The external seal which provides sealing between the main chamber and the rotating shaft and will prevent any gas or liquid leaks to the outside environment was provided and is available from, for example, John Crane Corp. and may be specified according to the pressure ratings and temperatures needed during the process. A cooling medium was coupled with the external seal to prevent overheating. The cooling liquid can be water or any other cooling medium such as glycol solutions. If contamination of the process is a concern, the solvent that is being processed in the rotating packed bed can be used as a cooling fluid for the seal. In the examples below, water was used as a cooling medium. The water goes through a finned forced-air heat exchanger to maintain desired cooling medium temperature Table 4 shows the available energy for moving the Rotating Packed Bed turbines as a function of different gas flowrates and feed pressures typical of gas processing plants. In most cases the amount of energy available is enough to completely supply the power required by the turbines.

Table 1 below shows examples of good $CO_2$ removal at various flow rates of $CO_2$ and methyl ethanolamine (MEA).

TABLE 1

| N2 Feed (SCFH) | CO2 Feed (SCFH) | Total Gas (SCFH) | MEA Flowrate (GPM) | CO2 Concentration Feed (vol %) | CO2 Concentration Product (vol %) | CO2 Removed % |
|---|---|---|---|---|---|---|
| 4000 | 210 | 4210 | 0.7 | 5 | 1.1 | 79 |
| 4000 | 210 | 4210 | 0.8 | 5 | 0.7 | 87 |
| | | | Increase CO2 vol % in feed (7.5 vol %) | | | |
| 4000 | 325 | 4325 | 1.1 | 7.5 | 1.2 | 80 |
| 4000 | 325 | 4325 | 1.6 | 7.5 | 0.7 | 91 |
| | | | Increase CO2 vol % in feed (10 vol %) | | | |
| 4000 | 446 | 4446 | 1.5 | 10 | 1.6 | 85 |
| 4000 | 446 | 4446 | 1.8 | 10 | 1.2 | 89 |

Table 2 shows reduction of $CO_2$ content in gas mixtures ranging from 5-10 vol % $CO_2$ down to less than 2 vol % (pipeline spec). The Height of Transfer Units numbers confirm superior mass transfer due to the process intensification.

TABLE 2

| N2 Feed (SCFH) | CO2 Feed (SCFH) | Total Gas (SCFH) | MEA Flowrate (GPM) | CO2 Concentration Feed (vol %) | CO2 Concentration Product (vol %) | Rich Loading mol CO2/mol MEA | Overall Mass Transfer Coefficient (Kla) (1/sec) | HTU (cm) | NTU (-) |
|---|---|---|---|---|---|---|---|---|---|
| 3000 | 158 | 3158 | 0.5 | 5 | 0.41 | 0.129 | 0.129 | 5.2 | 1.3 |
| 3000 | 158 | 3158 | 0.8 | 5 | 0.42 | 0.281 | 0.281 | 3.8 | 1.8 |
| 3000 | 158 | 3158 | 1 | 5 | 0.24 | 0.407 | 0.407 | 3.3 | 2.1 |

TABLE 2-continued

| N2 Feed (SCFH) | CO2 Feed (SCFH) | Total Gas (SCFH) | MEA Flowrate (GPM) | CO2 Concentration Feed (vol %) | CO2 Concentration Product (vol %) | Rich Loading mol CO2/mol MEA | Overall Mass Transfer Coefficient (Kla) (1/sec) | HTU (cm) | NTU (-) |
|---|---|---|---|---|---|---|---|---|---|
| | | | | Increase CO2 vol % in feed (7.5 vol %) | | | | | |
| 3000 | 242 | 3242 | 0.8 | 7.5 | 0.42 | 0.258 | 0.258 | 4.2 | 1.7 |
| 3000 | 242 | 3242 | 1.2 | 7.5 | 0.29 | 0.442 | 0.442 | 3.6 | 1.9 |
| 3000 | 242 | 3242 | 1.6 | 7.5 | 0.23 | 0.651 | 0.651 | 3.3 | 2.1 |
| | | | | Increase CO2 vol % in feed (10 vol %) | | | | | |
| 3000 | 446 | 3335 | 1.1 | 10 | 0.42 | 0.330 | 0.330 | 4.5 | 1.6 |
| 3000 | 446 | 3335 | 1.8 | 10 | 0.28 | 0.679 | 0.679 | 3.6 | 2.0 |

Table 3 shows that $CO_2$ removal tends to improve at higher rotating speeds which may be due to, for example, better mixing and/or thinner films.

TABLE 3

| | 1250 RPM | | 1500 RPM | | 1750 RPM | |
|---|---|---|---|---|---|---|
| CO2 Feed (Vol %) | ΔP (psi) | CO2 product (Vol %) | ΔP (psi) | CO2 product (Vol %) | ΔP (psi) | CO2 product (Vol %) |
| 7.5 | 4.2 | 1.4 | 4.8 | 1.0 | 5.1 | 1.0 |
| 10 | 4.4 | 2.1 | 5.0 | 1.2 | 5.4 | 1.2 |
| 15 | — | — | 5.1 | 2.1 | 5.5 | 1.7 |

Table 4. Available energy for moving the Rotating Packed Bed turbines as a function of different gas flowrates and feed pressures.

| Case | Liquid GPM | Specific Gravity | Supply Pressure | Discharge pressure | Available head | Efficiency | Max Avail. Shaft HP |
|---|---|---|---|---|---|---|---|
| 60 MMSCFD Gas Flowrate | 537.06 | 1 | 1500 | 20 | 3418.8 | 0.75 | 348 |
| | 537.06 | 1 | 1000 | 20 | 2263.8 | 0.75 | 230 |
| | 537.06 | 1 | 500 | 20 | 1108.8 | 0.75 | 113 |
| 120 MMSCFD Gas Flowrate | 905.07 | 1 | 1500 | 20 | 3418.8 | 0.75 | 586 |
| | 905.07 | 1 | 1000 | 20 | 2263.8 | 0.75 | 388 |
| | 905.07 | 1 | 500 | 20 | 1108.8 | 0.75 | 190 |
| 180 MMSCFD Gas Flowrate | 1206.7 | 1 | 1500 | 20 | 3418.8 | 0.75 | 781 |
| | 1206.7 | 1 | 1000 | 20 | 2263.8 | 0.75 | 517 |
| | 1206.7 | 1 | 500 | 20 | 1108.8 | 0.75 | 253 |

The claimed subject matter is not to be limited in scope by the specific embodiments described herein. Indeed, various modifications of the invention in addition to those described herein will become apparent to those skilled in the art from the foregoing description. Such modifications are intended to fall within the scope of the appended claims.

What is claimed is:

1. A system for removing an impurity from a feed gas stream, which system comprises:
   a rotating packed bed absorber with one or more rotatable packing rings, said absorber configured for contacting a feed gas stream comprising one or more impurities with a liquid to produce (i) an impurity-rich liquid solution having a pressure comprising one or more absorbed impurities and (ii) purified gas; and
   a pressure reducing device in fluid communication with the rotating packed bed absorber for receiving and reducing the pressure of the impurity-rich liquid solution and recovering energy therefrom and wherein at least some of the energy recovered in the pressure reducing device is employed to rotate the one or more rotatable packing rings of the rotating packed bed absorber wherein the rotating packed bed absorber comprises a liquid distributor comprising:
   (a) a pipe having a central conduit and an annulus about the conduit, the annulus is in fluid communication with a plurality of protruding tabs that extend into an interior region of the rotatable packing rings, the protruding tabs having a plurality of outlets for introducing liquid solution into the interior region, the central conduit in fluid communication with the interior region for removing a purified gas from the interior region; or
   (b) a pipe having a central conduit and an annulus about the conduit wherein one or more internal seals prevent feed gas from passing between the rotating packed bed and the pipe and wherein said internal seal comprises indentations sufficient to create a pressure drop within said space between the rotating packed bed and the pipe.

2. The system of claim 1, which further comprises a regenerator for regenerating the impurity-rich liquid solution by desorbing the impurity from the liquid solution, the regenerator is operably linked to the pressure reducing device and the packed bed absorber so that liquid solution can be directed to the rotating packed bed absorber for reuse.

3. The system of claim 2 wherein said regenerator comprises a rotating packed bed with one or more rotatable packing rings.

4. The system of claim 3 wherein the regenerator and pressure reducing device are configured such that at least some of the energy recovered in the pressure reducing device is employed in the regenerator.

5. The system of claim 1 wherein the pressure reducing device comprises a turbine, a control valve, or a combination thereof.

6. The system of claim 5 wherein the pressure reducing device comprises a turbine and control valve and wherein the turbine and rotating packed bed absorber each comprise a separate rotatable shaft.

7. The system of claim 5 wherein the pressure reducing device comprises a turbine and control valve and wherein the turbine and rotating packed bed absorber are operably connected to a common rotatable shaft.

8. A system for removing an impurity from a feed gas stream, which system comprises:
- a rotating packed bed absorber with one or more rotatable packing rings, said absorber configured for contacting a feed gas stream comprising one or more impurities with a liquid to produce (i) an impurity-rich liquid solution having a pressure comprising one or more absorbed impurities and (ii) purified gas; and
- a pressure reducing device in fluid communication with the rotating packed bed absorber for receiving and reducing the pressure of the impurity-rich liquid solution and recovering energy therefrom; and
- a regenerator for regenerating the impurity-rich liquid solution operably linked to the pressure reducing device for regenerating the impurity-rich liquid solution for reuse in the rotating packed bed absorber, wherein the regenerator and pressure reducing device are configured such that at least some of the energy generated in the pressure reducing device is employed in regeneration wherein the rotating packed bed absorber comprises a liquid distributor comprising:

(a) a pipe having a central conduit and an annulus about the conduit the annulus is in fluid communication with a plurality of protruding tabs that extend into an interior region of the rotatable packing rings, the protruding tabs having a plurality of outlets for introducing liquid solution into the interior region, the central conduit in fluid communication with the interior region for removing a purified gas from the interior region; or (b) a pipe having a central conduit and an annulus about the conduit wherein one or more internal seals prevent feed gas from passing between the rotating packed bed and the pipe and wherein said internal seal comprises indentations sufficient to create a pressure drop within said space between the rotating packed bed and the pipe.

9. The system of claim 8, which further comprises one or more additional, parallel connected rotating packed bed absorbers wherein the pressure reducing device comprises a turbine and wherein two or more rotating packed bed absorbers are operably connected to a common rotatable shaft.

10. The system of claim 8, wherein the regenerator comprises two or more parallel connected rotating packed bed regenerators and wherein the pressure reducing device comprises a turbine and wherein two or more rotating packed bed regenerators are operably connected to a common rotatable shaft.

11. The system of claim 8 wherein the regenerator comprises a packed tower.

12. The system of claim 8 wherein the rotating packed bed absorber comprises a liquid distributor comprising: a pipe having a central conduit and an annulus about the conduit, the annulus is in fluid communication with a plurality of protruding tabs that extend into an interior region of the rotatable packing rings, the protruding tabs having a plurality of outlets for introducing liquid solution into the interior region, the central conduit in fluid communication with the interior region for removing a purified gas from the interior region.

13. The system of claim 12 wherein the liquid distributor further comprises one or more internal seals to prevent feed gas from passing between the rotating packed bed and the pipe, wherein said internal seal comprises indentations sufficient to create a pressure drop within said space between the rotating packed bed and the pipe.

14. The system of claim 8 wherein the pressure reducing device comprises a turbine, a control valve, or a combination thereof.

15. The system of claim 14 wherein the pressure reducing device comprises a turbine and control valve and wherein the turbine and rotating packed bed absorber each comprise a separate rotatable shaft.

16. The system of claim 14 wherein the pressure reducing device comprises a turbine and control valve and wherein the turbine and rotating packed bed absorber are operably connected to a common rotatable shaft.

17. The system of claim 14, wherein the pressure reducing device comprises a turbine operably connected to the one or more rotatable packing rings of the rotating packed bed absorber such that at least some of the energy generated in the pressure reducing device is employed to rotate the one or more rotatable packing rings of the rotating packed bed absorber.

18. The system of claim 8 wherein the regenerator comprises a chamber, a rotating packed bed within the chamber, and a heater for heating at least a portion of the impurity-rich liquid solution.

19. The system of claim 18, wherein the heater is disposed within the chamber.

20. The system of claim 18, wherein the heater comprises a reboiler external to the chamber and a condenser.

* * * * *